United States Patent [19]

Poirier et al.

[11] 4,016,303

[45] Apr. 5, 1977

[54] METHOD OF FLOCKING BLOOD-CONTACTING SURFACES ON ARTIFICIAL IMPLANT DEVICES

[75] Inventors: Victor L. Poirier, Chelmsford; John T. Keiser, Acton, both of Mass.

[73] Assignee: The United States of America, Washington, D.C.

[22] Filed: Aug. 6, 1975

[21] Appl. No.: 602,385

[52] U.S. Cl. .................................. 427/2; 427/203; 427/206; 428/90; 3/1; 3/1.7; 128/1 D

[51] Int. Cl.² ..................... A61K 5/00; B05D 1/14; B05D 1/16; A61F 1/00

[58] Field of Search .............. 427/2, 203, 200, 352, 427/206, 337, 385, 430; 428/90, 288; 3/1, 1.4, 1.7; 128/334 R, 1 D, DIG. 3

[56] References Cited

UNITED STATES PATENTS

| | | | |
|---|---|---|---|
| 3,098,755 | 7/1963 | Barth et al. | 427/206 X |
| 3,956,553 | 5/1976 | Palmer et al. | 427/206 X |

OTHER PUBLICATIONS

"An Improved Blood–Pump Interface for Left–Ventricular Bypass," by William F. Bernard et al., Annals of Surgery, vol. 168, No. 4, Oct. 1968, pp. 750–764.

*Primary Examiner*—Ronald L. Frinks
*Attorney, Agent, or Firm*—Holman & Stern

[57] ABSTRACT

Blood-contacting surfaces of artificial implant devices which have been flocked with fibers of a blood-compatible polymeric material to promote formation of a stable and viable biological lining when the device has been implanted in a living body, are treated to strengthen the bonds between the fibers and the substrate surface and to interlock the fibers with each other so as to substantially reduce the possibility of fiber separation and release from the substrate surface into the blood stream. The treatment is effected by applying to the flocked surface a dilute solution of an adhesive material in a solvent therefor, the content of the adhesive material in the treating solution being controlled so as to be sufficient to coat the fibers only at their points of contact with each other and with the substrate surface. When the solvent is thereafter evaporated from the substrate surface, secondary bonds of adhesive material are formed at such points of contact, leaving the fibers otherwise uncoated so as not to interfere with their biological lining formation-promoting properties.

9 Claims, 4 Drawing Figures

METHOD OF FLOCKING BLOOD-CONTACTING SURFACES ON ARTIFICIAL IMPLANT DEVICES

BACKGROUND OF THE INVENTION

The present invention relates to artificial implant devices adapted to be implanted in blood-containing position in the bodies of living creatures such as human beings, and, more particularly, to the flocking of the blood-contacting surfaces of such devices to promote the formation of stable and viable biological linings on such surfaces.

In recent years, concentrated efforts have been made toward the development of various artificial implant devices for implantation in blood-contacting position in the human body, such as artificial heart devices and various blood circulatory assist devices. One of the problems encountered to connection with such long-term prosthetic devices is ensuring that the blood-contacting surfaces of such devices are sufficiently blood-compatible so as not to cause thrombosis, destruction of the formed elements in the blood, alteration of the plasma proteins, destruction of enzymes, depletion of electrolytes, adverse immune responses, damage to adjacent tissue, cancer, or toxic or allergic reactions. One approach to this problem has been the use of textured surfaces which will initiate deposition of fibrin from the blood to promote the formation of a stable and viable biological lining and which will provide secure anchoring for such lining. It has previously been proposed to form such textured surface by flocking the blood-contacting surfaces of such artificial implant devices with fibers of a blood-compatible polymeric material, such as polyester or nylon. In accordance with such proposal, the blood-contacting surface is first coated with a layer of suitable adhesive material, such as polyurethane adhesive, and thereafter the polymeric fibers, such as polyethylene terephthalate (Dacron) fibers, are applied to the adhesive-coated surface so as to adhesively secure the fibers to the surface.

While flocked surfaces formed in the above manner have been found to be effective in implanted devices for encouraging deposition of fibrin from the blood to promote the formation of a viable biological lining and for providing suitable anchoring for such lining, certain problems have been encountered which are attributable to fiber separation and release from the substrate surface into the blood stream, where they are transported to vital organs such as the kidneys and spleen. Investigations have shown that the weakening of the bonds between the polyester fibers and the substrate surface responsible for such release of fibers into the blood stream, is due primarily to the finish which must be applied to the polyester fibers to facilitate handling of the fibers during the flocking operation. Fibers without such finish applied thereto would agglomerate and prevent uniform application of the flock. When the fibers are applied to the adhesive-coated substrate surface, the fiber bonds are, at least partially, between the adhesive and the fiber finish rather than the polyester substrate. Such finish is at least somewhat soluble in water over a long period, and thus is capable of dissolving in contact with blood. If the device is implanted with the fiber finish still remaining on the flocked surface, the finish will be dissolved in vivo and transported to vital organs, such as the lungs, via the blood stream. To minimize the possibility of the finish dissolving in vivo, as much as possible of the fiber finish is preferably removed from the fibers after the flocking operation. In either event, however, the finish removal process, either in vivo or prior to implantation, will result in voids being formed at the spaces initially occupied by the finish. Such voids cause the bonds between the polyester fibers and the substrate surface to be weakened, leading to the fibers becoming separated from the substrate surface and being released into the blood stream.

SUMMARY OF THE INVENTION

It is accordingly a primary object of the present invention to provide the blood contacting surfaces of artificial implant devices with flocking of blood-compatible polymeric fibers which will remain firmly attached to such surfaces when the device is in implanted position.

In particular, it is an object of the present invention to provide a method of strengthening the bonds between such fibers and such surfaces and interlocking such fibers with each other so as to substantially reduce the possibility of fiber separation and release from such surfaces into the blood stream when the device is in implanted position.

Another object of the present invention is to provide a fiber-to-substrate surface bond strengthening method in accordance with the preceding object, which may be carried out subsequent to the steps of applying the flock to the substrate surface and removing from the fibers any antiagglomerating finish which would interfere with direct bonding of the fibers at their points of contact with each other and with the substrate surface.

A further object of the present invention is to provide a fiber-to-substrate surface bond strengthening method in accordance with the preceding objects, which will leave the fiber surfaces substantially uncoated so as not to interfere with their biological lining formation-promoting properties.

The above and other objects are achieved in accordance with the method of the present invention, which is carried out after the flock has been applied by known methods to the blood-contacting surfaces of an artificial implant device, and most advantageously, after any antiagglomerating fiber finish employed in the flocking operation has been removed from the fiber surfaces. In accordance with the method of the present invention, a dilute solution of adhesive material in a solvent therefor is applied to the flocked surface. The adhesive material becomes preferentially attracted by capillary action to the points of contact of the fibers with each other and with the substrate surface, filling the voids which were left by removal of the fiber finish. The content of adhesive material in the treating solution is controlled so as to be sufficient to coat the fibers only at these points of contact, so that when the solvent is subsequently evaporated from the flocked surface, secondary bonds of the adhesive material are formed at these points of contact, leaving the fiber surfaces otherwise uncoated so as not to interfere with their biological lining formationpromoting properties when the device is subsequently implanted. These secondary bonds strengthen the adhesion of the fibers to the substrate surface and interlock the fibers with each other, thereby substantially reducing the possibility of fiber separation and release from the substrate surface into the blood stream when the device is in implanted position in a living body.

BRIEF DESCRIPTION OF DRAWINGS

The invention is illustrated by way of example in the accompanying drawings which form part of this application and in which.

DESCRIPTION OF THE PREFERRED EMBODIMENTS

Figure 1:
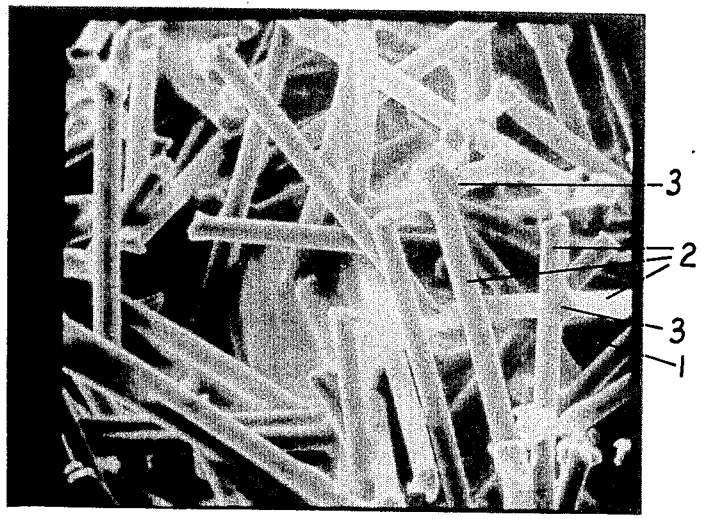
FIG. 1 is a scanning electron photomicrograph of a polyurethane surface flocked with polyethylene terephthalate fibers and subsequently treated with the bond strengthening method in accordance with the present invention, at 200 magnification.

The flocked surfaces which are treated in accordance with the method of the present invention, may be prepared by known techniques, which do not form a part of the present invention. For example, a blood-compatible substrate surface, which is typically a polyurethane, a silicone, or stainless steel coated with a suitable polymeric primer, is first coated with a hydrolytically stable blood-compatible adhesive material, such as a cross-linking polyurethane adhesive or a silicone-based adhesive, and thereafter fibers of a blood-compatible polymeric material, such as nylon or, more typically, a polyester such as polyethylene terephthalate (Dacron), are applied to the adhesive-coated surface. The surface is then dried to remove the solvent from the adhesive and heated to cure the adhesive material, thereby adhesively securing the fibers to the substrate surface. The finish which is initially on the surface of the fibers to facilitate handling of the fibers and prevent agglomeration of the fibers during the flocking operation, is then generally removed from the fibers, typically by washing in a boiling alkaline bath.

The flocked surfaces are treated in accordance with the method of the present invention by applying thereto a dilute solution of a blood-compatible adhesive material in a suitable solvent therefor. The adhesive material employed in this step of the process is advantageously the same adhesive material as was employed in the flocking operation, preferably a cross-linking polyester diisocyanate polyurethane adhesive, but in a more diluted form. For example, whereas a polyurethane adhesive material used in the flocking operation typically has a polyurethane solids content of approximately 50 percent by volume, the diluted solution of polyurethane adhesive employed in this step of the method of the present invention should have a polyurethane solids content within the range of from 5 to 20 percent by volume. Although the particular solvent employed for diluting the adhesive material is not critical, and may include, for example, dimethyl formamide or acetone, the preferred solvent for use with polyurethane adhesive material is methylethyl ketone due to its very low water content. Water, a common impurity in some organic solvents, reacts with the NCO groups in the polyurethane to form urea bonds (false bonds) and carbon dioxide gas, which could produce porosity and degradation of the adhesive.

The dilute solution of adhesive material is applied to the flocked surface preferably by dipping the flocked surface into the solution. Other application techniques, such as brushing or spraying, can also be employed if desired. When the dilute solution of the adhesive material is applied to the flocked surface, the adhesive material is preferentially attracted by capillary action to the points of contact of the fibers with each other and with the substrate surface, thereby filling the voids left as a result of removal of the finish from the fiber surfaces. The content of adhesive material in the solution should be controlled so as to be sufficient to coat the fibers only at such points of contacts, since it is of fundamental importance that the major portion of the fibers remain uncoated so as not to interfere with their biological lining formation-promoting properties. In the preferred embodiment of the invention, the adhesive-containing solution is a solution of polyurethane in a solvent such as methylethyl ketone, having a polyurethane content of from 5 to 20 percent, most preferably 10 percent, by volume. This content of polyurethane in the solution will be sufficient to coat the fibers only at their points of contact with each other and with the substrate surface, leaving the major portion of the fibers uncoated.

After the dilute adhesive solution is applied to the flocked surface, the solvent is evaporated from the surface and the adhesive material is cured. This results in the formation of secondary bonds of adhesive material at the points of contact of the fibers with each other and with the substrate surface, the major portion of the fibers remaining uncoated and in a form suitable for promoting the development of a stable and viable biological lining when implanted in blood-contacting position in a living body. The secondary bonds of adhesive material formed at the points of contact of the fibers with each other and with the substrate surface strengthen the adhesion of the fibers to the substrate surface and interlock the fibers with each other, thereby substantially reducing the possibility of fiber separation and release from the substrate surface into the blood stream where implanted in blood-contacting position in a living body.

The method of the present invention is illustrated by way of the following example.

EXAMPLE

Two identical molded polyurethane bladders for use as elastomeric pumping chambers in implantable left and right ventricular bypass pumps, were treated in the following manner. The bladders were internally coated with a 50 percent by volume solids solution of a cross-linking polyester diisocyanate polyurethane adhesive in a methylethyl ketone solvent. The adhesive-coated surfaces wee then flocked with 3 denier per filament fibers of polyethylene terephthalate, the fibers having an average diameter of 25 microns and an average length of 250 microns. The fiber surfaces were provided with an anti-agglomerating finish to render them free-flowing and facilitate their handling during the flocking operation. The bladder surfaces were then dried to remove the solvent from the adhesive, and the adhesive was then cured by heating in an oven at 110°

C for 4 hours. The fiber finish was then removed from the fiber surfaces by washing in a boiling alkaline bath.

One of the flocked bladders (bladder A) was then treated in accordance with the present invention as follows. The flocked bladder was dipped in a 10 percent by volume solids solution in methylethyl ketone solvent of the same polyurethane adhesive as was employed in the flocking operation described above. The bladder was then removed from the solution and dried to evaporate the solvent from the adhesive, and the adhesive was then cured by heating in an oven at 110° C for 4 hours.

Figure 2:
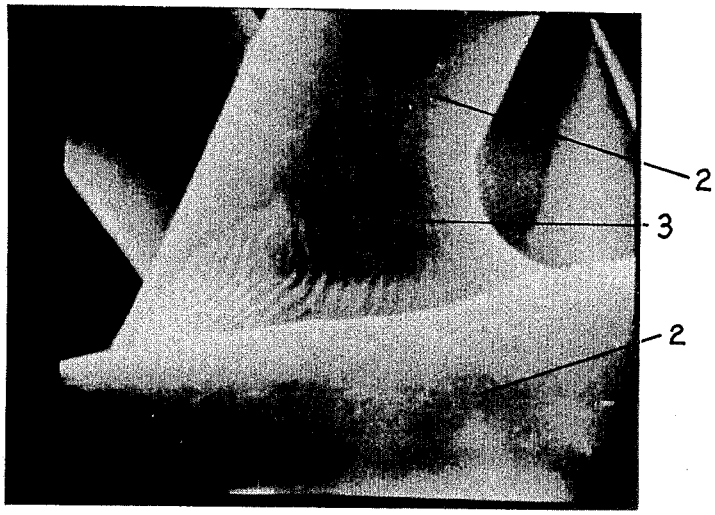
FIG. 2 is a scanning electron photomicrograph of the same flocked surface as in FIG. 1, at 2,000 magnification, showing a bond at a typical contact point between two fibers.
Figure 3:
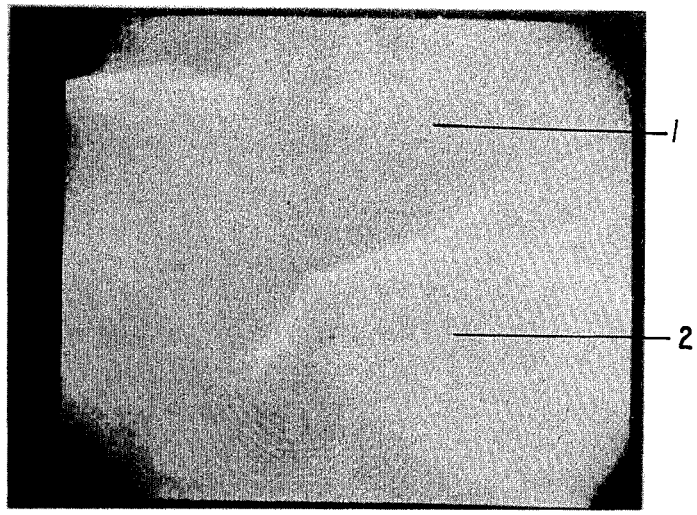
FIG. 3 is a scanning electron photomicrograph of the same flocked surface as in FIG. 1, at 2,000 magnification, showing a bond at a typical contact point between a fiber and the substrate surface.
Figure 4:
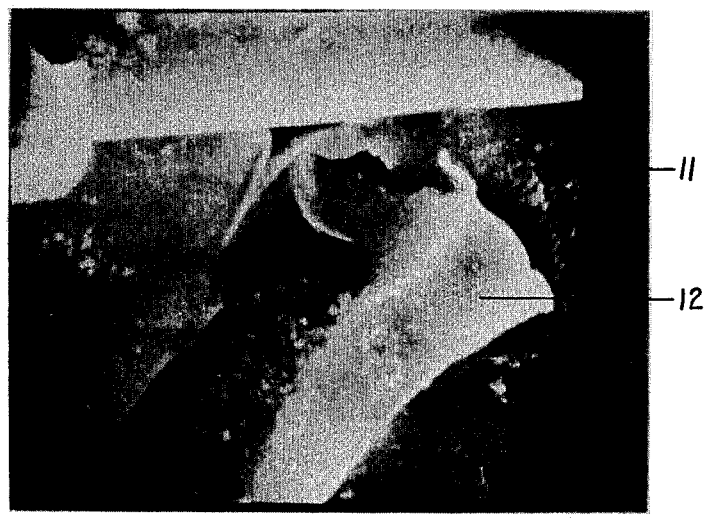
FIG. 4 is a scanning electron photomicrograph of a polyurethane surface flocked with polyethylene terephthalate fibers, without the bond strengthening treatment of the present invention, at 2,000 magnification, showing a bond at a typical contact point between a fiber and the substrate surface.

Scanning electron photomicrograph of the resulting flocked surface of bladder (A) are shown in FIGS. 1, 2 and 3, FIG. 1 being at 200 magnification, FIG. 2 being at 2,000 magnification and showing the bond at a typical contact point between two fibers, and FIG. 3 being at 2,000 magnification and showing the bond at a typical contact point between a fiber and the substrate surface. As shown in the photomicrographs, excellent bonds were formed between the substrate surface 1 and the flock fibers 2, and additional bonds were formed by fillets 3 of the adhesive material at points of contact between adjacent fibers. The fiber surfaces otherwise remained uncoated. By way of comparison, FIG. 4 is a scanning electron photomicrograph, at 2,000 magnification, of the flocked surface of bladder (B), i.e., the other bladder flocked as above but not subsequently treated in accordance with the method of the present invention. As shown in FIG. 4, the flocked surface of bladder (B) is characterized by poor bonding between the substrate surface 11 and the flocked fibers 12.

Each of the bladders (A) and (B) were subjected to the following test to quantitatively determine flock release from the flocked surface of the bladder. The flocked surface area of each bladder was determined to be 73 cm$^2$. The test consisted of submerging the flocked bladder in a container filled with 730 ml of water, providing 10 ml of water for every 1 cm$^2$ of flocked surface area. The container was mounted on a "shake" table and oscillated for 5 minutes, thereby providing much more severe agitation than would be encountered in actual in vivo application of the bladder. The bladder was then removed from the water, and the water was immediately transferred to another container containing a grid with major divisions of 1 cm$^2$ and minor divisions of 1 mm$^2$. The water level was maintained at 1 cm above the grid. With this system, each cm$^2$ of grid was covered by 1 ml of water. The number of fibers which appeared in each square centimeter of area represented those fibers released from 0.1 cm$^2$ of flocked surface area on the bladder. With bladder (B), which had not been treated in accordance with the method of the present invention, the test results indicated approximately 650 fibers released per cm$^2$ of flocked surface or a total of approximately 50,000 fibers. On the other hand, with bladder (A), which had been treated in accordance with the method of the present invention, the test results showed that in a volume of 10 ml of water, only one or two fibers were found present. It can be concluded from this test that there was practically no flock release from the bladder treated in accordance with the method of the present invention.

Bladder (A) was used as the elastomeric pumping chamber in an implantable ventricular bypass pump which was implanted in a calf for in vivo evaluation. The animal recovery and behavior were quite normal after implantation and no physiological complications arose. After two weeks, the animal was sacrificed and the flocked bladder surface was carefully studied. It was found that a very uniform biological layer had been formed on the flocked bladder surface.

The embodiments of the invention in which an exclusive property or privilege is claimed are defined as follows:

1. In a method for the manufacture of an artificial implant device adapted to be implanted in blood-contacting position in the body of a living creature such as a human being, said method including the steps of flocking the bloodcontacting surface of said device with fibers of a bloodcompatible polymeric material by first applying to said surface a coating of blood-compatible adhesive material and thereafter applying said fibers to the adhesive-coated surface so as to adhesively secure said fibers to said surface, the improvement whereby the bonds between said fibers and said surface are strengthened and said fibers are interlocked with each other so as to substantially reduce the possibility of fiber separation and release from said surface when said device is in implanted position, comprising the steps of applying to said flocked surface a dilute solution of said adhesive material in a solvent therefor whereby said adhesive material is preferentially attracted by capillary action to the points of contact of said fibers with each other and with said surface, the content of said adhesive material in said solution being sufficient to coat said fibers only at said points of contact, and thereafter evaporating said solvent from said surface to thereby form secondary bonds of said adhesive material at said points of contact and leave said fibers otherwise uncoated.

2. The method of claim 1, wherein said fibers are polyester fibers.

3. The method of claim 2, wherein said fibers are polyethylene terephthalate fibers.

4. The method of claim 1, wherein said dilute solution of adhesive material is applied to said flocked surface by dipping said flocked surface into said solution.

5. The method of claim 1, wherein said adhesive material is a polyurethane.

6. The method of claim 5, wherein said solvent is methylethyl ketone.

7. The method of claim 5, wherein the polyurethane content in said dilute solution is from 5 to 20 percent by volume.

8. The method of claim 7, wherein the polyurethane content in said dilute solution is 10 percent by volume.

9. The method of claim 1, wherein said fibers are provided with an anti-agglomerating surface finish to facilitate their handling during the flocking operation, and said finish is removed from said fibers after the flocking operation and prior to applying said dilute solution of adhesive material to said flocked surface.

* * * * *